(12) United States Patent
Kuwabara

(10) Patent No.: US 11,342,745 B2
(45) Date of Patent: May 24, 2022

(54) SWITCHED-MODE POWER SUPPLY AND MEDICAL SYSTEM WITH A SWITCHED-MODE POWER SUPPLY

(71) Applicant: TDK CORPORATION, Tokyo (JP)

(72) Inventor: Hideyuki Kuwabara, Tokyo (JP)

(73) Assignee: TDK CORPORATION, Tokyo (JP)

( * ) Notice: Subject to any disclaimer, the term of this patent is extended or adjusted under 35 U.S.C. 154(b) by 107 days.

(21) Appl. No.: 16/822,547

(22) Filed: Mar. 18, 2020

(65) Prior Publication Data

US 2020/0313426 A1 Oct. 1, 2020

(30) Foreign Application Priority Data

Mar. 25, 2019 (JP) .............................. JP2019-057457

(51) Int. Cl.
| | |
|---|---|
| *H02M 1/08* | (2006.01) |
| *H02H 9/04* | (2006.01) |
| *H02H 1/00* | (2006.01) |
| *H02H 7/12* | (2006.01) |
| *H02M 1/32* | (2007.01) |
| *H02M 1/00* | (2006.01) |
| *A61B 8/00* | (2006.01) |
| *A61B 6/00* | (2006.01) |

(52) U.S. Cl.
CPC ............ *H02H 9/04* (2013.01); *H02H 1/0007* (2013.01); *H02H 7/1213* (2013.01); *H02M 1/0009* (2021.05); *H02M 1/08* (2013.01); *H02M 1/32* (2013.01); *A61B 6/56* (2013.01); *A61B 8/56* (2013.01)

(58) Field of Classification Search
CPC ...... H02H 1/0007; H02H 7/1213; H02H 9/04; H02M 1/08; H02M 1/0009; H02M 1/32; H02M 3/00; A61B 8/56; A62B 6/56
See application file for complete search history.

(56) References Cited

U.S. PATENT DOCUMENTS

| | | | | |
|---|---|---|---|---|
| 7,379,284 B2 * | 5/2008 | Fukushi | .................. | H02M 1/32 361/94 |
| 2005/0078424 A1 * | 4/2005 | Yamamura | .............. | H02M 1/32 361/91.1 |

FOREIGN PATENT DOCUMENTS

| | | |
|---|---|---|
| CN | 106953406 A * | 7/2017 |
| JP | 2001-119933 A | 4/2001 |

* cited by examiner

*Primary Examiner* — Kyle J Moody
*Assistant Examiner* — Jye-June Lee
(74) *Attorney, Agent, or Firm* — Oliff PLC

(57) ABSTRACT

A switching power supply includes: a DC-DC converter including a switching element and configured to output electric power input from an input terminal to an output terminal; a current detector configured to detect a load current output to the output terminal and to output a voltage corresponding to the load current as a detection result; a time constant circuit having a predetermined charging time constant; a time constant circuit controller configured to be connected to the current detector and the time constant circuit and configured to output a charging current based on the detection result to charge the time constant circuit or discharge charge charged in the time constant circuit as a discharging current on based on a comparison between the detection result output by the current detector and a reference voltage.

12 Claims, 6 Drawing Sheets

SWITCHED-MODE POWER SUPPLY AND MEDICAL SYSTEM WITH A SWITCHED-MODE POWER SUPPLY

CROSS-REFERENCE TO RELATED APPLICATION

Priority is claimed on Japanese Patent Application No. 2019-057457, filed Mar. 25, 2019, the content of which is incorporated herein by reference.

BACKGROUND OF THE INVENTION

Field of the Invention

The present invention relates to a switching power supply and a medical system.

Description of Related Art

In the related art, a technology in which a current exceeding a rated value of a switching power supply (a so-called peak current) can be output is described (for example, refer to Patent Document 1).
[Patent Document]
[Patent Document 1] Japanese Unexamined Patent Application, First Publication No. 2001-119933

SUMMARY OF THE INVENTION

In the above-mentioned related art, a time during which the peak current can be output is set to prevent a power supply device and a load from being damaged due to the flowing peak current. It is desirable that the time during which the peak current can be output be relatively long as long as it is possible to prevent a power supply device and a load from being damaged. Here, when a current value of the peak current is relatively small, the energy is small and an influence on the power supply device and the load is also small. Thus, it is possible to set the time during which the peak current can be output to be longer than in a case in which a current value of the peak current is relatively large. However, according to the related art, the time during which the peak current can be output is fixed in accordance with a case in which a peak current with a relatively large current value flows. Thus, the time during which the peak current can be output is shortened even if the current value of the peak current is relatively small.

The present invention was made in view of such circumstances, and an object of the present invention is to provide a switching power supply and a medical system capable of variably controlling a time during which a peak current can be output in accordance with a magnitude of the peak current.

An aspect of the present invention is a switching power supply which includes: an input terminal configured to be connected to an input power supply; an output terminal configured to be connected to a load; a DC-DC converter unit including a switching element and configured to output electric power input from the input terminal to the output terminal; a current detection unit configured to detect a load current output to the output terminal and to output a voltage corresponding to the load current as a detection result; a time constant circuit unit having a predetermined charging time constant; a time constant circuit control unit configured to be connected to the current detection unit and the time constant circuit unit and configured to output a charging current based on the detection result to charge the time constant circuit unit or discharge charge charged into the time constant circuit unit as a discharging current on the basis of a comparison between the detection result output by the current detection unit and a reference voltage; and a switching control unit configured to control the switching element of the DC-DC converter unit on the basis of a control output of the time constant circuit unit.

According to the present invention, it is possible to variably control a time during which a peak current can be output in accordance with a magnitude of the peak current.

DETAILED DESCRIPTION OF THE INVENTION

First Embodiment

An embodiment of the present invention will be described below with reference to the drawings.

Figure 1:
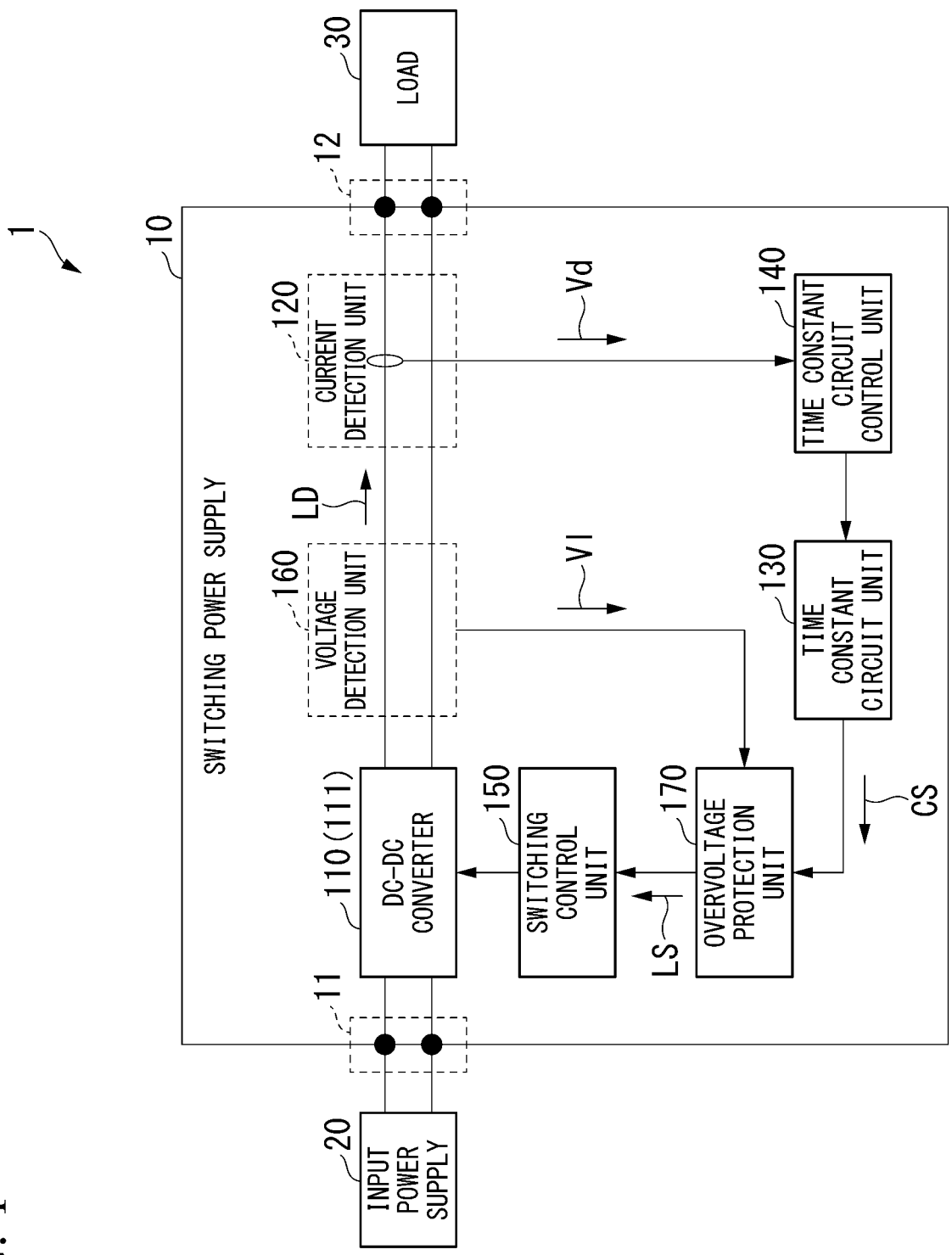
FIG. 1 is a diagram showing an example of a constitution of a system according to an embodiment.

FIG. 1 is a diagram showing an example of a constitution of a system 1 according to the embodiment. The system 1 includes a switching power supply 10, an input power supply 20, and a load 30.

The input power supply 20 supplies electric power (direct current (DC) electric power or alternating current (AC) electric power) to the switching power supply 10.

The load 30 operates using electric power supplied from the input power supply 20 via the switching power supply 10.

[Functional Constitution of Switching Power Supply 10]

The switching power supply 10 includes an input terminal 11, an output terminal 12, a DC-DC converter unit 110, a current detection unit 120, a time constant circuit unit 130, a time constant circuit control unit 140, a switching control unit 150, a voltage detection unit 160, and an overvoltage protection unit 170.

The input terminal 11 is connected to the input power supply 20. Electric power is supplied from the input power supply 20 to the input terminal 11. In an example of the embodiment, the input power supply 20 is connected to the input terminal 11 using an electric power supply wiring.

When the input power supply 20 supplies AC electric power, the switching power supply 10 includes a rectifying circuit unit (not shown) and converts AC electric power to be supplied into DC electric power.

The DC-DC converter unit 110 includes a switching element 111 (not shown), converts electric power supplied to the input terminal 11 and outputs the converted electric power from the output terminal 12.

The output terminal 12 is connected to the load 30 and outputs electric power supplied from the DC-DC converter unit 110 to the load 30.

The current detection unit 120 detects a load current LD output to the output terminal 12 and outputs a voltage corresponding to the load current LD as a detection result. In this example, the current detection unit 120 includes a voltage output type current sensor and outputs a current detection voltage Vd based on a value of the detected load current LD as a detection result.

Although a case in which the current detection unit 120 detects a current of the load current LD on a high potential side wiring has been described in the embodiment, the present invention is not limited thereto. The current detection unit 120 may detect a current of the load current LD on a low potential side wiring. Furthermore, the current detection unit 120 may detect the load current LD using a shunt resistor or a current transformer.

The time constant circuit unit 130 has a predetermined charging time constant tc. In this example, the time constant circuit unit 130 includes a so-called CR series circuit.

The time constant circuit control unit 140 controls a state of charge ST of the time constant circuit unit 130. To be more specific, the time constant circuit control unit 140 is connected to the current detection unit 120 and the time constant circuit unit 130. The time constant circuit control unit 140 discharges charge charged into the time constant circuit unit 130 as a discharging current Id car outputs a charging current Ic based on the current detection voltage Vd to charge the time constant circuit unit 130 on the basis of comparison between the current detection voltage Vd output by the current detection unit 120 and a reference voltage Vs.

An example of a more specific circuit constitution of the time constant circuit unit 130 and the time constant circuit control unit 140 will be described with reference to FIG. 2.

[Example of Circuit Constitution of Time Constant Circuit Unit 130 and Time Constant Circuit Control Unit 140]

Figure 2:
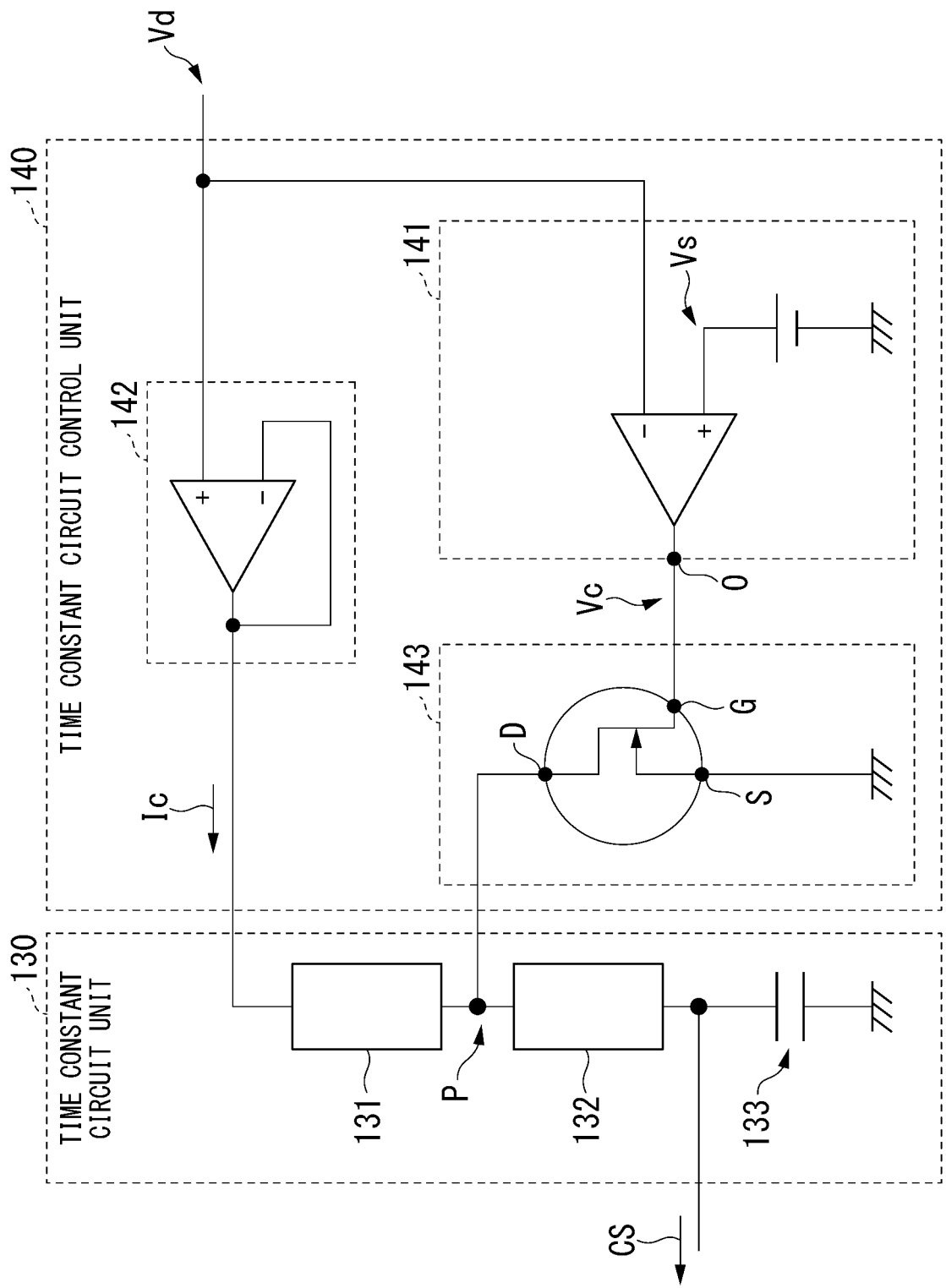
FIG. 2 is a diagram showing an example of a circuit constitution of a time constant circuit unit and a time constant circuit control unit in the embodiment.

FIG. 2 is a diagram showing an example of a circuit constitution of the time constant circuit unit 130 and the time constant circuit control unit 140 in the embodiment.

The time constant circuit unit 130 includes a current limiting resistor 131, a resistor 132, and a capacitor 133. The current limiting resistor 131, the resistor 132, and the capacitor 133 constitute a CR series circuit.

The time constant circuit control unit 140 includes a comparator unit 141, a voltage follower unit 142, and a switch unit 143.

The switch unit 143 includes a switch element such as a field effect transistor (FET) and includes a gate terminal G, a source terminal S, and a drain terminal D. Although a case in which the switch unit 143 includes an n-type FET as a switch element has been described in this example, a conduction state between the source terminal S—the drain terminal D may change between an on state and an off state in accordance with a change in output state of the comparator unit 141 and the form is not limited.

The switch unit 143 has the source terminal S grounded and the drain terminal D connected to a connection point P between the current limiting resistor 131 and the resistor 132 in the switching power supply 10.

The comparator unit 141 outputs a switch control voltage Vc based on a result of comparing the current detection voltage Vd with the reference voltage Vs. To be more specific, in the comparator unit 141, the reference voltage Vs is input to a non-inverting input terminal and the current detection voltage Vd output from the current detection unit 120 is input to an inverting input terminal. An output terminal O of the comparator unit 141 is connected to the gate terminal G of the switch unit 143. The comparator unit 141 outputs a result of comparing the voltages from the output terminal O as the switch control voltage Vc.

The voltage follower unit 142 includes a differential amplifier constituted as a so-called voltage follower and outputs the charging current Ic based on the current detection voltage Vd output from the current detection unit 120 to the time constant circuit unit 130.

[Operation Example of Time Constant Circuit Control Unit 140]

First, a case in which a magnitude of the load current LD exceeds a rated value (that is, a case in which the peak current flows) will be described.

Figure 3:
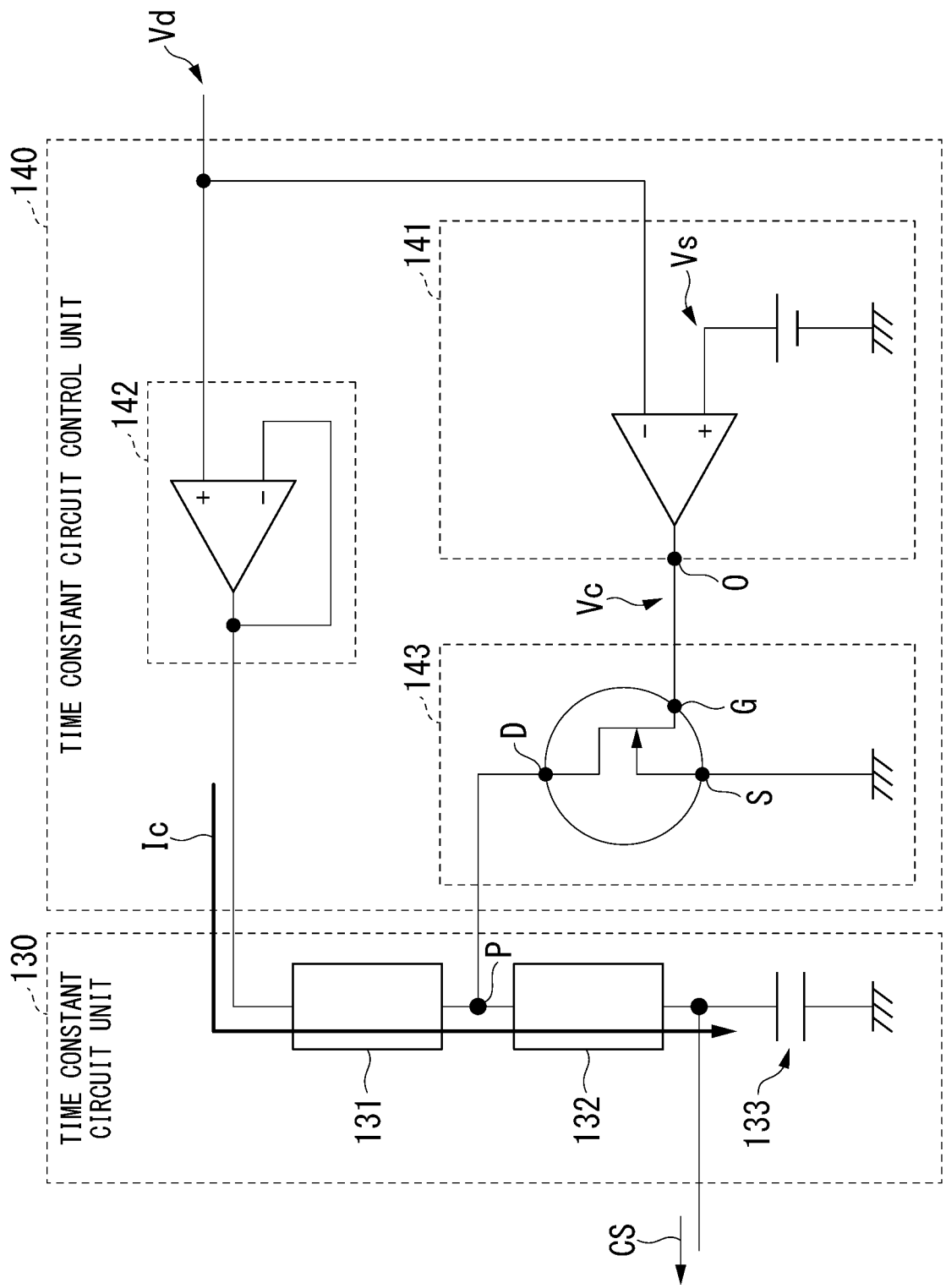
FIG. 3 is a diagram showing an example of a circuit operation at the time of charging the time constant circuit unit in the embodiment.

FIG. 3 is a diagram showing an example of a circuit operation at the time of charging the time constant circuit unit 130 in the embodiment. In this case, the value of the current detection voltage Vd output by the current detection unit 120 is larger than a value of the reference voltage Vs (that is, the current detection voltage Vd exceeds the reference voltage Vs).

When the peak current flows, the comparator unit 141 sets the switch control voltage Vc to a low potential (L) and outputs the set switch control voltage Vc so that the switch unit 143 is in an off state.

The voltage follower unit 142 outputs the charging current Ic with a magnitude based on the current detection voltage Vd to the time constant circuit unit 130. The charging current Ic output from the voltage follower unit 142 flows into the capacitor 133 via the current limiting resistor 131, the connection point P, and the resistor 132.

As a result, charge is charged to the capacitor 133 at a charging rate based on a magnitude of the charging current Ic and a charging time constant tc of the time constant circuit unit 130. A control output CS of a voltage based on an amount of charge charged into the capacitor 133 is output from the time constant circuit unit 130.

At this time, when the value of the load current LD detected in the current detection unit 120 increases, the charging current Ic increases and a charging rate with respect to the capacitor 133 increases.

A case in which a magnitude of the load current LD does not exceed a rated value (that is, a case in which the load current LD with a current value smaller than the peak current flows) will be described below.

Figure 4:
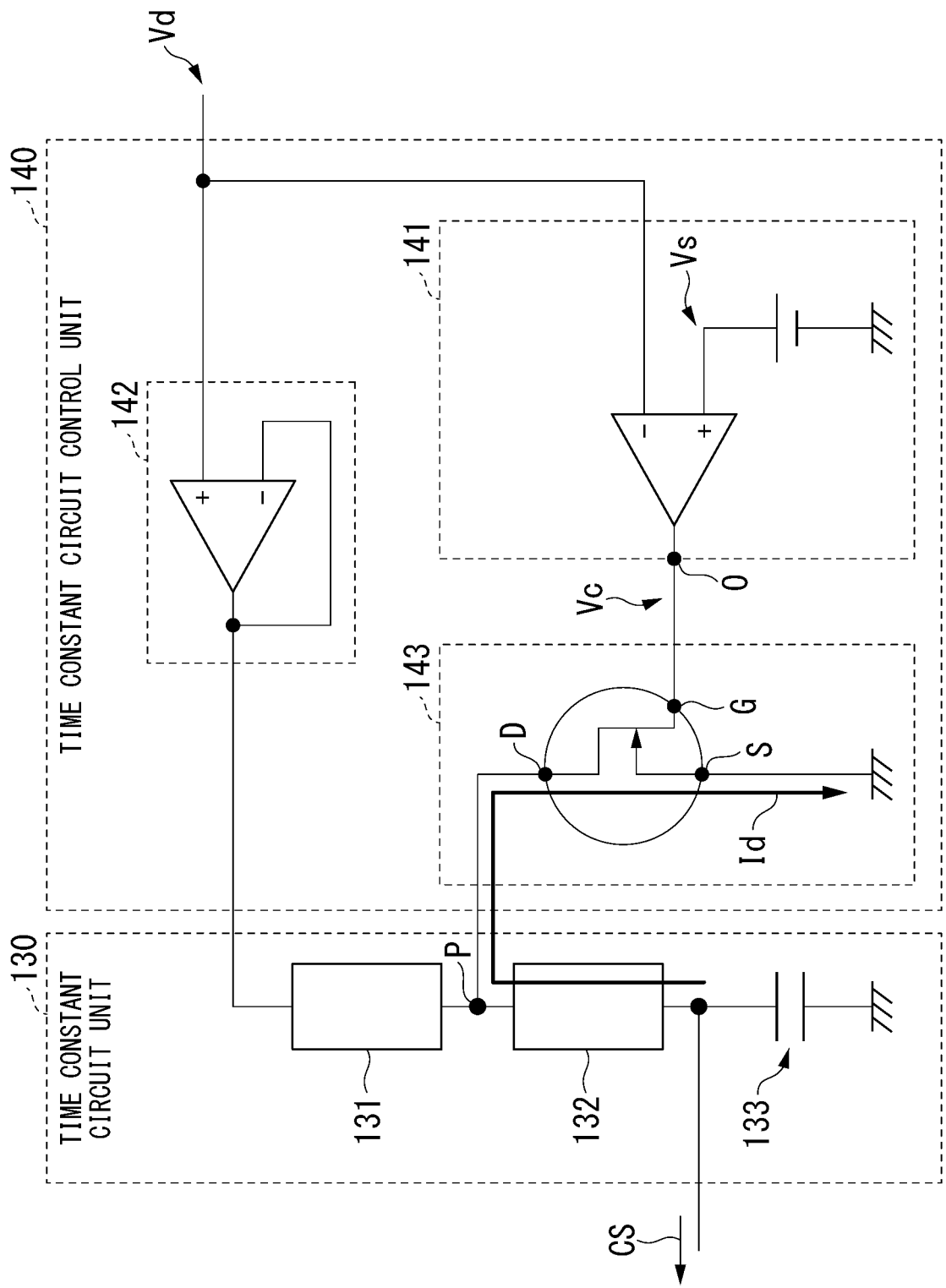
FIG. 4 is a diagram showing an example of the circuit operation at the time of discharging the time constant circuit unit in the embodiment.

FIG. 4 is a diagram showing an example of a circuit operation at the time of discharging the time constant circuit unit 130 in the embodiment. In this case, a value of the current detection voltage Vd output by the current detection unit 120 is equal to or lower than a value of the reference voltage Vs (that is, the current detection voltage Vd is equal to or lower than the reference voltage Vs). When the load current LD with a current value smaller than that of the peak current flows, the comparator unit 141 sets the switch control voltage Vc to a high potential (H) and outputs the set switch control voltage Vc so that the switch unit 143 is in an on state.

As a result, charge charged into the capacitor 133 is discharged using the discharging current Id flowing via the resistor 132, the connection point P, the drain terminal D, and the source terminal S.

In summary, the time constant circuit control unit 140 is connected, to the current detection unit 120 and the time constant circuit unit 130 and outputs the charging current Ic based on the current detection voltage Vd to charge the time constant circuit unit 130 or discharges charge charged into the time constant circuit unit 130 as the discharging current Id on the basis of a comparison between the current detection voltage Vd output by the current detection unit 120 and the reference voltage Vs.

Also, the switch unit 143 is connected to the time constant circuit unit 130 and performs a selection between charging the time constant circuit unit 130 by supplying the charging current Ic output by the voltage follower unit 142 to the time constant circuit unit 130 and discharging charge charged into the time constant circuit unit 130 as the discharging current Id on the basis of the switch control voltage Vc output by the comparator unit 141.

Here, depending on whether the switch unit 143 is in an on state or in an off state, an impedance of the time constant circuit unit 130 expected from the current detection voltage Vd changes. To be specific, when the switch unit 143 is in an off state, the current limiting resistor 131, the resistor 132, and the capacitor 133 are connected in series. Furthermore, when the switch unit 143 is in an on state, the resistor 132 and the capacitor 133 are in a bypassed state. In this case, an impedance of the time constant circuit unit 130 expected from the current detection voltage Vd when the switch unit 143 is in an on state is relatively lower than that when the switch unit 143 is in an off state.

Here, if the voltage follower unit 142 is not provided and a change in impedance of the time constant circuit unit 130 due to a change in on/off state of the switch unit 143 appears as a potential change of the inverting input terminal of the comparator unit 141 in a circuit constitution in which the inverting input terminal of the comparator unit 141 and the current limiting resistor 131 are directly connected, a comparison result (the switch control voltage Vc) as an output of the comparator unit 141 varies in accordance with a change in on/off state of the switch unit 143 in some cases. That is to say, when the voltage follower unit 142 is not provided, a change in impedance of the time constant circuit unit 130 due to a change in state of the switch unit 143 affects a comparison result (the switch control voltage Vc) of the comparator unit 141 in some cases.

As described above, the time constant circuit control unit 140 in the embodiment includes the voltage follower unit 142. The time constant circuit control unit 140 supplies the charging current Ic from the current detection unit 120 to the time constant circuit unit 130 via the voltage follower unit 142.

The voltage follower unit 142 prevents a change in impedance of the time constant circuit unit 130 from being transmitted to a circuit on the inverting input terminal side of the comparator unit 141. In other words, the voltage follower unit 142 minimizes an influence of a change in impedance of the time constant circuit unit 130 due to a change in state of the switch unit 143 on a comparison result of the comparator unit 141. The voltage follower unit 142 is an example of a circuit constitution of a mutual influence minimizing unit.

An interaction minimizing unit may not be constituted as the above-described voltage follower circuit. The mutual influence minimizing unit may have any circuit constitution as long as the time constant circuit unit 130 and a circuit on the input terminal (in this example, the inverting input terminal) side of the comparator unit 141 can be configured to be separated in terms of impedance. For example, the mutual influence minimizing unit may be configured as an emitter follower circuit using an active element such as a transistor.

When the interaction minimizing unit is configured of an active element, it is possible to supply the charging current Ic obtained by amplifying a current output from the current detection unit 120 even if a current value output from the current detection unit 120 is insufficient to charge the time constant circuit unit 130.

Referring to FIG. 1 again, the control output CS output from the time constant circuit unit 130 is supplied to the overvoltage protection unit 170.

The voltage detection unit 160 detects an output voltage of the DC-DC converter unit 110. The voltage detection unit 160 outputs a detection voltage value V1 indicating the detected output voltage to the overvoltage protection unit 170. The overvoltage protection unit 170 limits an output of the DC-DC converter unit 110 on the basis of the detection voltage value V1 of the voltage detection unit 160 and the state of charge ST of the time constant circuit unit 130. For example, the overvoltage protection unit 170 outputs an output limiting signal LS to the switching control unit 150 to limit an output of the DC-DC converter unit 110.

Here, when the detection voltage value V1 exceeds a predetermined threshold value voltage (that is, when an output of the switching power supply 10 is an overvoltage), the overvoltage protection unit 170 limits the output of the DC-DC converter unit 110. Furthermore, when the capacitor 133 of the time constant circuit unit 130 is charged and the control output CS exceeds a predetermined threshold value voltage, the overvoltage protection unit 170 limits the output of the DC-DC converter unit 110.

That is to say, the overvoltage protection unit 170 limits the output of the DC-DC converter unit 110 in both the case of an overvoltage and when the control output CS exceeds a predetermined threshold value voltage.

The switching control unit 150 limits the output of the DC-DC converter unit 110 on the basis of the output limiting signal LS output by the overvoltage protection unit 170 to control the switching element 111 in the DC-DC converter unit 110.

As described above, the output limiting signal LS is output on the basis of the control output CS based on the state of charge ST of the time constant circuit unit 130. That is to say, the switching control unit 150 controls the switching element 111 in the DC-DC converter unit 110 on the basis of the control output CS of the time constant circuit unit 130.

Summary of First Embodiment

Generally, when a load current LD with a magnitude exceeding a design value (for example, a peak current) flows, heat generated in the switching power supply 10 and the load 30 due to the load current LD is minimized by limiting the output of the DC-DC converter unit 110.

The switching power supply 10 in the embodiment charges the capacitor 133 in the time constant circuit unit 130 using the charging current Ic based on a detection result (for example, the current detection voltage Vd) of the load current LD. The time constant circuit unit 130 outputs the control output CS based on a state of charge ST of the capacitor 133. The overvoltage protection unit 170 does not limit the output of the DC-DC converter unit 110 when the control output CS is equal to or lower than the predetermined threshold value voltage and limits the output of the DC-DC converter unit 110 when the control output CS exceeds the predetermined threshold value voltage. In the switching power supply 10 in the embodiment, when the load current LD increases, the charging current Ic increases and a rate of increase of the control output CS increases. When the rate of increase of the control output CS increases, a timing at which the overvoltage protection unit 170 limits the output of the DC-DC converter unit 110 becomes earlier. That is to say, the overvoltage protection unit 170 limits the output of the DC-DC converter unit 110 in accordance with a reaction rate based on a detection result of the load current LD.

Therefore, according to the switching power supply 10 in the embodiment, when a peak current flows, it is possible to limit the output of the DC-DC converter unit 110 at the reaction rate based on a magnitude of the peak current.

For this reason, according to the switching power supply 10 in the embodiment, when a relatively large peak current flows, the output of the DC-DC converter unit 110 is limited at a relatively early timing and when a relatively small peak current flows, the output of the DC-DC converter unit 110 is limited at a relatively late timing.

According to the switching power supply 10 in the embodiment constituted in this way, it is possible to variably control a time during which the peak current can be output in accordance with the magnitude of the peak current.

Here, as a conventional general constitution, it is also possible to variably change a time at which the peak current can be output in accordance with the magnitude of the peak current by providing a comparator and a time constant circuit for each stage of a peak current value. However, according to a conventional general constitution, when a comparator and a time constant circuit are provided for each stage of the peak current value, the size of a circuit is increased and the dimensions of a device increase in some cases.

According to the switching power supply 10 in the embodiment, since the switching power supply 10 can be constituted of one comparator unit 141 (or an operational amplifier 144) and one time constant circuit unit 130, the size of a circuit is not increased and the dimensions of the switching power supply 10 can be reduced.

In the switching power supply 10 in the embodiment, the switching power supply 10 may have a constitution in which the switching power supply 10 does not include the overvoltage protection unit 170. When the switching power supply 10 does not include the overvoltage protection unit 170, the time constant circuit unit 130 outputs the control output CS to the switching control unit 150. The switching control unit 150 controls the switching element 111 in the DC-DC converter unit 110 on the basis of the control output CS. That is to say, even in such a constitution, the switching control unit 150 controls the switching element 111 in the DC-DC converter unit 110 on the basis of the state of charge ST of the time constant circuit unit 130.

[Modification]

Figure 5:
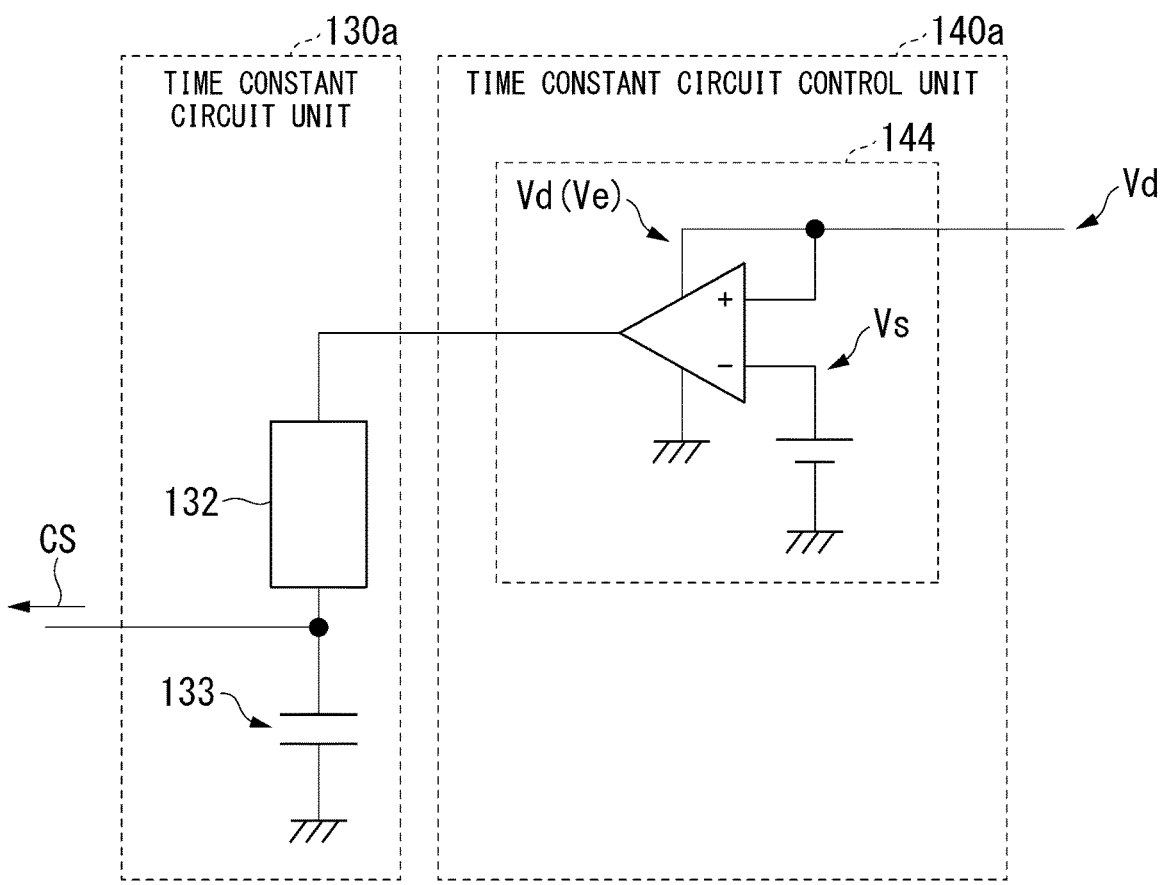
FIG. 5 is a diagram showing a modification of the time constant circuit control unit and the time constant circuit unit in the embodiment.

FIG. 5 is a diagram showing a modification of the time constant circuit control unit and the time constant circuit unit in the embodiment. A time constant circuit unit 130a includes a CR series circuit. The time constant circuit unit 130a and the above-described time constant circuit unit 130 differ in that the current limiting resistor 131 is omitted in the CR series circuit. Although a case in which the current limiting resistor 131 is omitted will be described in this example, a constitution in which the current limiting resistor 131 is not omitted may be provided.

A time constant circuit control unit 140a includes an operational amplifier 144. The operational amplifier 144 operates by setting a voltage based on a current detection voltage Vd to a power supply voltage Ve, supplies a charging current Ic based on the current detection voltage Vd to the time constant circuit unit 130a, and charges and discharges the time constant circuit unit 130a by switching between the charging current Ic and a discharging current Id in accordance with the current detection voltage Vd.

It is also possible to variably control a time during which a peak current can be output in accordance with a magnitude of the peak current using a switching power supply 10 including the time constant circuit unit 130a and the time constant circuit control unit 140a constituted in this way.

Second Embodiment

Figure 6:
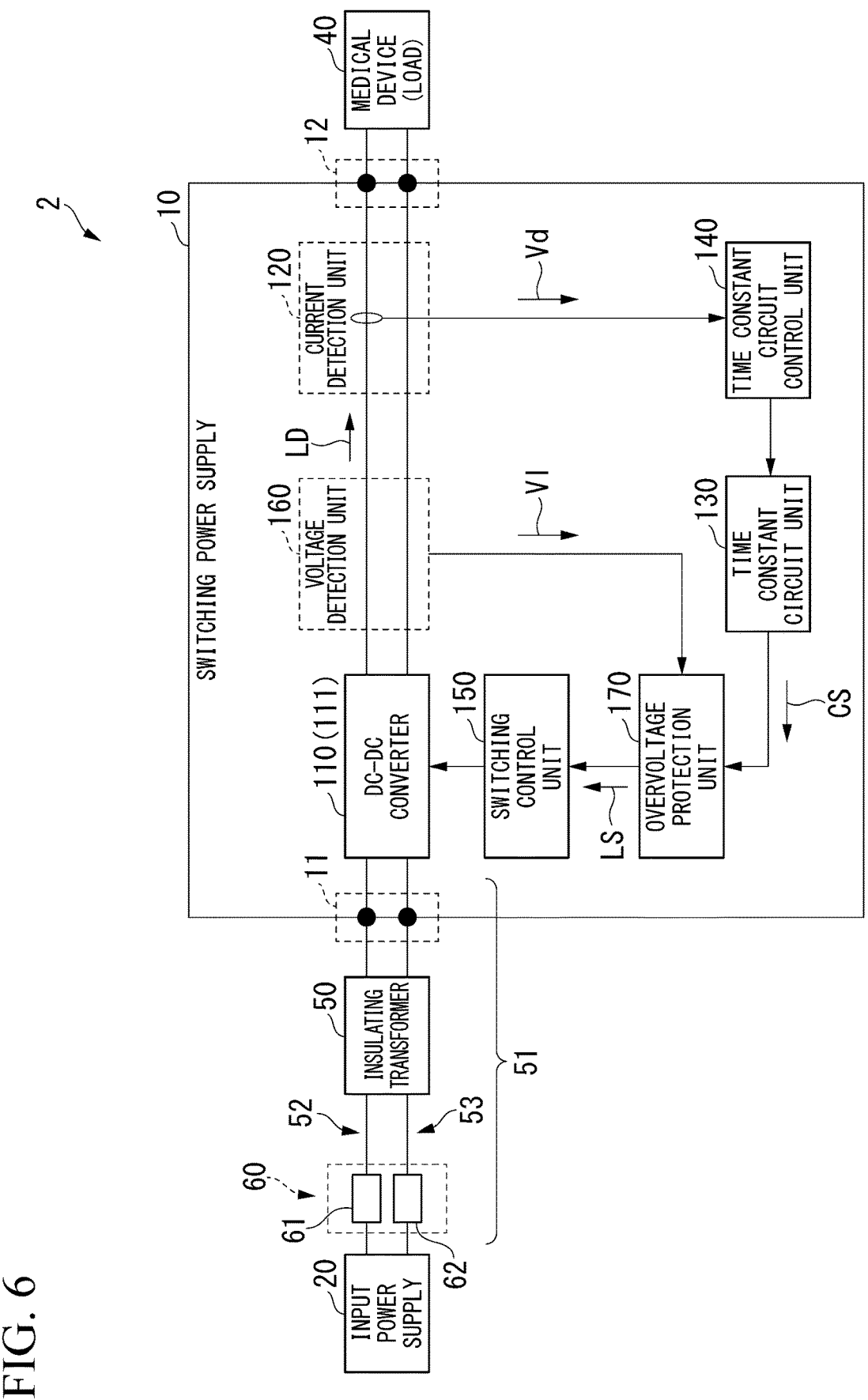
FIG. 6 is a diagram showing an example of a constitution of a medical system according to an embodiment.

FIG. 6 is a diagram showing an example of a constitution of a medical system 2 according to an embodiment. In the medical system 2, a medical device 40 is connected to a switching power supply 10 as a load instead of the above-described load 30. Furthermore, the system 2 and the above-described system 1 differ in that an insulating transformer 50 and an overcurrent cutoff unit 60 are provided between an input power supply 20 and the switching power supply 10. Constituent elements of the system 2 that are the same as those of the above-described system 1 will be denoted with reference numerals that are the same as those of the system 1 and description thereof will be omitted.

Examples of the medical device 40 include a wide range of devices such as general medical machines such as a nebulizer and a blood gas analyzing device, managed medical machines such as an X-ray imaging device, an electrocardiograph, and an ultrasonic diagnostic device, highly managed medical machines such as an artificial dialysis instrument, an infusion pump, an automatic peritoneal perfusion device, an artificial heart-lung device, a component blood sampling device, an artificial respirator, and the like. The medical device 40 is connected to an output terminal 12 as a load 30.

The overcurrent cutoff unit 60 includes, for example, a circuit breaker, a fuse, and the like and cuts off an overcurrent. The overcurrent cutoff unit 60 includes a first overcurrent cutoff unit 61 and a second overcurrent cutoff unit 62. The first overcurrent cutoff unit 61 is disposed on a high potential line 52 side of a primary wiring 51 in the switching power supply 10. The second overcurrent cutoff unit 62 is disposed on a low potential line 53 side of the primary wiring 51.

Positions at which the insulating transformer 50 and the overcurrent cutoff unit 60 are disposed shown in FIG. 6 are examples and the present invention is not limited thereto. For example, the switching power supply 10 may have a constitution in which the switching power supply 10 itself has the insulating transformer 50 and the overcurrent cutoff unit 60 provided therein.

Also, when the input power supply 20 supplies AC electric power, the switching power supply 10 includes an L-phase wiring (one wiring) and an N-phase wiring (the other wiring) as the primary wiring 51. In this case, the first overcurrent cutoff unit 61 is disposed on the L-phase wiring (one wiring) side of the primary wiring 51 in the switching power supply 10 and the second overcurrent cutoff unit 62 is disposed on the N-phase wiring (the other wiring) side of the primary wiring 51.

Since the medical system 2 constituted in this way also includes the above-described switching power supply 10, it is possible to variably control a time during which a peak current can be output in accordance with a magnitude of the peak current.

Although the embodiments of the present invention have been described in detail above with reference to the drawings, the specific constitution is not limited to the embodiments and it is possible to appropriately change the specific constitution without departing from the gist of the present invention. The above-described constitution may be combined with each of the above-described embodiments.

Each of the units included in each of the devices in the above-described embodiments may be realized using dedicated hardware or may be realized using a memory and a microprocessor.

Each of the units included in each of the devices may be constituted of a memory and a central processing unit (CPU) and a program configured to realize a function of each of the units included in each of the devices may be loaded into a memory and executed to realize the function.

Also, processes using each of the units included in the control unit may be performed by recording a program configured to realize a function of each of the units included in each of the devices on a computer-readable recording medium, causing a computer system to read the program recorded on the recording medium, and executing the program. A "computer system" mentioned herein includes an operating system (OS) and hardware such as peripheral devices.

Also, the "computer system" includes a homepage providing environment (or a display environment) when a WWW system is used.

In addition, the "computer-readable recording medium" refers to a portable medium such as a flexible disk, a magneto-optical disk, a read only memory (ROM), and a compact disk (CD)-ROM and a storage device such as a hard disk built in a computer system. Moreover, the "computer-readable recording medium" includes a medium configured to dynamically hold a program for a short period of time such as a communication line when a program is transmitted via a network such as the Internet or a communication circuit such as a telephone circuit and a medium configured to hold a program for a certain period of time such as a volatile memory inside a computer system serving as a server or a client in this case. Furthermore, the above-described program may be a program configured to realize a part of the function or a program which can realize the above-described function in combination with a program recorded in a computer system in advance.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description and is only limited by the scope of the appended claims.

EXPLANATION OF REFERENCES

1 System
2 Medical system
10 Switching power supply
110 DC-DC converter unit
120 Current detection unit
130, 130a Time constant circuit unit
140 140a Time constant circuit control unit
141 Comparator unit
142 Voltage follower unit
143 Switch unit
143, 144 Operational amplifier
150 Switching control unit
160 Voltage detection unit
170 Overvoltage protection unit

What is claimed is:

1. A switching power supply, comprising:
an input terminal configured to be connected to an input power supply;
an output terminal configured to be connected to a load;
a DC-DC converter unit including a switching element and configured to output electric power input from the input terminal to the output terminal;
a current detection unit configured to detect a load current output to the output terminal and to output a voltage corresponding to the load current as a detection result;
a time constant circuit unit having a predetermined charging time constant;
a time constant circuit control unit configured to be connected to the current detection unit and the time constant circuit unit and configured to output a charging current based on the detection result to charge the time constant circuit unit or discharge charge charged into the time constant circuit unit as a discharging current based on a comparison between the detection result output by the current detection unit and a reference voltage, the time constant circuit control unit including:
a comparator unit configured to output a switch control voltage based on a result of the comparison between the detection result and the reference voltage; and
a switch unit configured to be connected to the time constant circuit unit and configured to perform a selection between charging the time constant circuit unit by supplying the charging current corresponding to the load current detected by the current detection unit to the time constant circuit unit; and discharging charge charged into the time constant circuit unit as the discharging current based on the switch control voltage output by the comparator unit; and
a switching control unit configured to control the switching element of the DC-DC converter unit based on a control output of the time constant circuit unit.

2. The switching power supply according to claim 1, wherein the time constant circuit control unit includes a mutual influence minimizing unit configured to minimize an influence of a change in impedance of the time constant circuit unit due to a change in state of the switching element on a comparison result of the comparator unit, and
the time constant circuit control unit supplies the charging current from the current detection unit to the time constant circuit unit via the mutual influence minimizing unit.

3. The switching power supply according to claim 2, comprising:
a voltage detection unit configured to detect an output voltage of the DC-DC converter; and
an overvoltage protection unit configured to output an output limiting signal for limiting an output of the DC-DC converter to the switching control unit based on a detection voltage value of the voltage detection unit and a control output of the time constant circuit unit,
wherein the switching control unit limits the output of the DC-DC converter based on the output limiting signal output by the overvoltage protection unit to control the switching element of the DC-DC converter.

4. A medical system, comprising:
the switching power supply according to claim 3;

a medical device configured to be connected to the output terminal as a load;
an insulating transformer configured to electrically insulate between the input terminal and the output terminal;
a first overcurrent cutoff unit disposed on one side of a primary wiring of the switching power supply; and
a second overcurrent cutoff unit disposed on an other side of the primary wiring.

5. A medical system, comprising:
the switching power supply according to claim 2;
a medical device configured to be connected to the output terminal as a load;
an insulating transformer configured to electrically insulate between the input terminal and the output terminal;
a first overcurrent cutoff unit disposed on one side of a primary wiring of the switching power supply; and
a second overcurrent cutoff unit disposed on an other side of the primary wiring.

6. The switching power supply according to claim 1, comprising:
a voltage detection unit configured to detect an output voltage of the DC-DC converter; and
an overvoltage protection unit configured to output an output limiting signal for limiting an output of the DC-DC converter to the switching control unit based on a detection voltage value of the voltage detection unit and a control output of the time constant circuit unit,
wherein the switching control unit limits the output of the DC-DC converter based on the output limiting signal output by the overvoltage protection unit to control the switching element of the DC-DC converter.

7. A medical system, comprising:
the switching power supply according to claim 6;
a medical device configured to be connected to the output terminal as a load;
an insulating transformer configured to electrically insulate between the input terminal and the output terminal;
a first overcurrent cutoff unit disposed on one side of a primary wiring of the switching power supply; and
a second overcurrent cutoff unit disposed on an other side of the primary wiring.

8. A medical system, comprising:
the switching power supply according to claim 1;
a medical device configured to be connected to the output terminal as a load;
an insulating transformer configured to electrically insulate between the input terminal and the output terminal;
a first overcurrent cutoff unit disposed on one side of a primary wiring of the switching power supply; and
a second overcurrent cutoff unit disposed on an other side of the primary wiring.

9. A switching power supply, comprising:
an input terminal configured to be connected to an input power supply;
an output terminal configured to be connected to a load;
a DC-DC converter unit including a switching element and configured to output electric power input from the input terminal to the output terminal;
a current detection unit configured to detect a load current output to the output terminal and to output a voltage corresponding to the load current as a detection result;
a time constant circuit unit having a predetermined charging time constant;
a time constant circuit control unit configured to be connected to the current detection unit and the time constant circuit unit and configured to output a charging current based on the detection result to charge the time constant circuit unit or discharge charge charged into the time constant circuit unit as a discharging current based on a comparison between the detection result output by the current detection unit and a reference voltage, the time constant circuit control unit including an operational amplifier configured to operate by setting a voltage based on the detection result to a power supply voltage, supply the charging current based on the detection result to the time constant circuit unit, and charge and discharge the time constant circuit unit by switching between the charging current and the discharging current in accordance with the detection result; and
a switching control unit configured to control the switching element of the DC-DC converter unit based on a control output of the time constant circuit unit,
wherein one of input terminals of the operational amplifier and one of power supply terminals of the operational amplifier are connected, and the voltage based on the detection result is input to both the one of the input terminals and the one of the power supply terminals.

10. The switching power supply according to claim 9, comprising:
a voltage detection unit configured to detect an output voltage of the DC-DC converter; and
an overvoltage protection unit configured to output an output limiting signal for limiting an output of the DC-DC converter to the switching control unit based on a detection voltage value of the voltage detection unit and a control output of the time constant circuit unit,
wherein the switching control unit limits the output of the DC-DC converter based on the output limiting signal output by the overvoltage protection unit to control the switching element of the DC-DC converter.

11. A medical system, comprising:
the switching power supply according to claim 10;
a medical device configured to be connected to the output terminal as a load;
an insulating transformer configured to electrically insulate between the input terminal and the output terminal;
a first overcurrent cutoff unit disposed on one side of a primary wiring of the switching power supply; and
a second overcurrent cutoff unit disposed on an other side of the primary wiring.

12. A medical system, comprising:
the switching power supply according to claim 9;
a medical device configured to be connected to the output terminal as a load;
an insulating transformer configured to electrically insulate between the input terminal and the output terminal;
a first overcurrent cutoff unit disposed on one side of a primary wiring of the switching power supply; and
a second overcurrent cutoff unit disposed on an other side of the primary wiring.

* * * * *